United States Patent
Aidun

(10) Patent No.: US 8,452,460 B2
(45) Date of Patent: May 28, 2013

(54) FLUIDICS-BASED ORIENTATION AND SORTING DEVICE FOR PLANT EMBRYOS

(75) Inventor: Cyrus K. Aidun, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 417 days.

(21) Appl. No.: 12/937,244

(22) PCT Filed: Apr. 9, 2009

(86) PCT No.: PCT/US2009/039982
§ 371 (c)(1), (2), (4) Date: Oct. 8, 2010

(87) PCT Pub. No.: WO2009/126758
PCT Pub. Date: Oct. 15, 2009

(65) Prior Publication Data
US 2011/0153093 A1 Jun. 23, 2011

Related U.S. Application Data

(60) Provisional application No. 61/043,867, filed on Apr. 10, 2008.

(51) Int. Cl.
*G05D 11/00* (2006.01)
(52) U.S. Cl.
USPC .......................................................... 700/282
(58) Field of Classification Search
USPC .......................................................... 700/282
See application file for complete search history.

(56) References Cited

U.S. PATENT DOCUMENTS

| 5,284,765 | A * | 2/1994 | Bryan et al. | 435/420 |
| 6,684,564 | B1 * | 2/2004 | Hirahara | 47/57.6 |
| 2002/0192040 | A1 * | 12/2002 | McKinnis | 406/181 |
| 2004/0224301 | A1 * | 11/2004 | Timmis et al. | 435/4 |

FOREIGN PATENT DOCUMENTS

| EP | 1498025 A2 * | 1/2005 |
| EP | 1498025 A3 | 2/2005 |

OTHER PUBLICATIONS

International Search Report and Written Opinion received for PCT Patent Application No. PCT/US2009/039982, mailed on Jul. 31, 2009, 11 pages.
Belmonte et al., "Alterations of the glutathione redox state improve apical meristem structure and somatic embryo quality in white spruce (*Picea glauca*)", Journal of Experimental Botany, vol. 56, No. 419, Sep. 2005, pp. 2355-2364.

* cited by examiner

*Primary Examiner* — Mohammad Ali
*Assistant Examiner* — Sivalingam Sivanesan
(74) *Attorney, Agent, or Firm* — Morrison & Foerster LLP

(57) ABSTRACT

The present invention provides an apparatus for fluidics-based automated orientation of plant embryos. The apparatus comprises flow channels, flow direction means, an orientation detector and a control unit. The orientation of embryos suspended in liquid flowing individually through the flow channels is constrained to cotyledon-first or cotyledon-last orientation by dimensional constraints. The orientation is determined by the orientation detector. Embryos not oriented as desired are directed into a reservoir tube by the flow direction means, after which the flow is directed from the reservoir tube to the outlet thereby having reoriented the embryo. Means of sorting viable embryos from other objects are optionally included in the apparatus.

14 Claims, 6 Drawing Sheets a b c d

FLUIDICS-BASED ORIENTATION AND SORTING DEVICE FOR PLANT EMBRYOS

CROSS REFERENCE TO RELATED APPLICATIONS

This application is a U.S. National Phase patent application of PCT/US2009/039982, filed Apr. 9, 2009, which claims priority to U.S. Provisional patent application Ser. No. 61/043,867, filed Apr. 10, 2008, all of which are hereby incorporated by reference in the present disclosure in their entirety.

BACKGROUND TO THE INVENTION

General Introduction to Problem Area

Somatic embryogenesis in plants is a process in which somatic embryos are formed from an initial explant being a cell in a plant tissue. The somatic embryos formed are genetically identical copies of the plant providing the initial explant. The process of somatic embryogenesis thereby offers a tool to obtain large numbers of genotypically identical plants for multiplication of selected genotypes of commercial interest, for conservation of endangered species or for generating genetically uniform plant material for research purposes.

Physiological Background to the Procedures Related to the Problem

To produce plants from somatic embryos of conifers, a multi-step procedure is applied to meet the physiological needs of the different stages of development as described below and shown in FIG. 1. Initiation of somatic embryogenesis starts with induction of somatic embryos from an initial explant, typically an immature zygotic embryo, on a solidified culture medium containing plant growth regulator. Somatic embryos continue to form, typically on the same composition culture medium, and a proliferating embryogenic culture form. At the proliferating stage, several of the key features generally regarded as beneficial for the process of somatic embryogenesis process, take place: (i) the mass propagation of genotypically identical propagules through unlimited multiplication of immature somatic embryos; (ii) cryogenic storage of proliferating embryos substantiates an virtually eternal store of clones, i.e. a clone bank is established, (iii) transgenic modification of the immature somatic embryo allow for large scale propagation of genetically improved propagules. At the next step in the procedure, the proliferating somatic embryo is subjected to a growth medium that triggers embryo development to progress into the maturation stage. Conversion from proliferation to maturation only occurs in a fraction of the proliferating embryos in the culture. Low conversion rates are encountered more frequently in genotypes from recalcitrant conifer species, but are common in all conifer species as well as other plant species. The manual labour needed to collect embryos increase with the decrease in conversion rate, and thereby the cost and risk of contamination and other inaccuracies. Low conversion rate from proliferation to maturation is a major bottleneck for commercial large scale applications of somatic embryogenesis procedures. For germination, mature somatic embryos are subjected to different culture regimes to induce root- and shoot formation, in a number of different steps; desiccation, sucrose treatment, red light induction, and blue light stimulation. Thereafter, germinated embryos deemed appropriately developed are transferred to a compost material and gradually transferred to an environment ex vitro during which the sucrose content is reduced. The different treatments during germination into a plant requires repeated manual handling of individual germinants and plants adding a considerable cost to the overall procedure.

Production of Plants from Somatic Embryos

The prior art procedure for producing plants from somatic embryos requires manual handling at several steps making the procedure time consuming, expensive and inaccurate.

For conifer species, standard procedures used involve several steps when manual handling is required. The general procedure is outlined in FIG. 1 (see e.g. von Arnold S, Clapham D. Spruce embryogenesis. 2008. *Methods Mol Biol.* 2008; 427:31-47; Belmonte M F, Donald G, Reid D M, Yeung E C and Stasolla C. 2005. Alterations of the glutathione redox state improve apical meristem structure and somatic embryo quality in white spruce (*Picea glauca*). *J Exp Bot*, Vol. 56, No. 419, pp. 2355-2364).

There are four steps that rely on manual handling to obtain a small plant from the mature somatic embryo as seen in FIG. 1. The first manual interaction is when [1] the mature embryo is isolated from immature embryos (120), and placed horizontally in a plastic container under sterile conditions; the second [2] occur after 3-7 days of resting (130), then mature embryo is transferred to a gelled culture medium for initiation of germination processes. The germinated somatic embryo will under appropriate culture medium composition and light conditions initiate roots (140). The third manual transfer [3] is when the germinant having a small root formed is transferred to an upright position with the root partially immersed in liquid germination media (150). The fourth [4] and final transfer is when the germinated embryos has a tap root and small lateral roots, then it is transferred into a solid substrate in a pot for further plant formation (160).

TABLE 1

List of designations pertaining to FIG. 1.

| Item | Designation |
|---|---|
| 100 | Mature embryo |
| 101 | Crown of a mature embryo |
| 102 | Foot of a mature embryo |
| 103 | Width of crown of a mature embryo |
| 104 | Length of a mature embryo |
| 120 | Maturation phase |
| 130 | Resting phase |
| 140 | Germination phase |
| 150 | In vitro plant formation phase |
| 160 | Ex vitro plant formation phase |

Conversion from proliferation to maturation only occurs in a fraction of the proliferating embryos in the culture. Low conversion rates are encountered more frequently in genotypes from recalcitrant conifer species, but are common in all conifer species as well as other plant species. The manual labour needed to collect embryos increase with the decrease in conversion rate, and thereby the cost and risk of contamination and other inaccuracies. Low conversion rate from proliferation to maturation is a major bottleneck for commercial large scale applications of somatic embryogenesis procedures. For germination, mature somatic embryos are subjected to different culture regimes to induce root- and shoot formation, in a number of different steps; desiccation, sucrose treatment, red light induction, and blue light stimulation. Thereafter, germinated embryos deemed appropriately developed are transferred to a compost material and gradually transferred to an environment ex vitro during which the sucrose content is reduced. The different treatments during germination into a plant requires repeated manual handling of individual germinants and plants adding a considerable cost to the overall procedure.

Plant embryos can be suspended into a liquid to facilitate automated processing. However, the liquid-suspended embryos become randomly oriented and need to be oriented properly at planting.

U.S. Pat. No. 5,284,765A discloses a method of orienting plant embryos. The properly desiccated embryos are suspended in a benign liquid flotation medium having a density in the range of about 1.059-1.104 g/cm3. The density must be adjusted empirically so that a predominant number of viable embryos will float and nonviable embryos will sink. In at least the case of conifer somatic embryos, they will float with the end bearing the latent cotyledons upward. After sufficient separation time in the flotation medium the oriented embryos are swept by a flowing liquid stream into a conduit. They enter cotyledon end first and are then carried to a delivery point without losing that orientation. Here they are separated from the transporting medium. The embryos, still positioned cotyledon end first, may then be picked up by robotic or other means for further processing, such as insertion into an artificial seed. However, the method is laborious e.g. in that the density of the flotation medium needs to be experimentally determined. Also, the sorting of viable and nonviable embryos is quite inexact.

US2002192040A discloses apparatus and methods useful for introducing a desired spacing between or classifying and sorting objects, e.g. plant embryos. Objects carried serially in a fluid stream enter the apparatus via an upstream conduit. A sensor associated with the conduit provides information regarding an object at a particular location in the upstream conduit and produces a signal. A switch coupled to the upstream conduit directs the fluid stream to a downstream conduit designated for a certain type of object in response to the signal by applying a force to a conduit, e.g., by aligning the upstream conduit with a downstream conduit to create a fluid-tight path. However, the apparatus does not provide means of orientating the embryos.

It would be desirable to obtain a means for efficient and accurate orientation of embryos. The present invention relates to an apparatus which allows automatization of the step of orienting the embryos correctly prior to planting. It is an object of the invention to provide an automated apparatus for orienting plant embryos.

SUMMARY OF THE INVENTION

The present invention provides an alternative, improved apparatus for automated orientation of plant embryos such as somatic plant embryos. An apparatus having additional capability of sorting acceptable embryos from other objects is also provided.

Apparatus for automatic orienting of plant embryos suspended in a liquid flowing though the apparatus is disclosed, comprising:
   a) flow channels for the liquid comprising liquid inlet (1) of an inlet tube (2), liquid outlet (3) of an outlet tube (4), reservoir tube (5) connected to a reservoir device (6), said reservoir device comprising means for generating positive liquid pressure in relation to the liquid pressure at outlet (3), means for accommodating liquid flowing in as well as means of providing liquid for outward flow, wherein the inlet tube (2), the outlet tube (4) and the reservoir tube (5) are connected at an intersection (7), and wherein the flow channels are dimensioned such that embryos may travel with the liquid flowing though the channels but are restricted to travelling either in a crown-first or crown-last orientation by dimensional constraints without a possibility to change orientation while travelling through any of the said tubes unless the change in orientation occurs as disclosed further below;
   b) flow direction means (18) comprising means of:
      i) directing the flow from the inlet (1) to the outlet (3);
      ii) directing the flow from the inlet (1) to the reservoir device (6); and
      iii) directing the flow from the reservoir device (6) to the outlet (3);
   c) detector(s) comprising an orientation detector (10) placed in the inlet tube (2), wherein the orientation detector (10) comprises means of determining the orientation of an embryo passing though the inlet tube (2);
   d) control unit (17) for steering the flow of the liquid in the flow channels comprising means of receiving input from the orientation detector (10) and means controlling the flow direction means (18) such that:
      i) in a default position, when no embryo is detected by the orientation detector (10), the flow direction means (18) is controlled such that the flow of the liquid in the flow channels is directed from the inlet (1) to the outlet (3);
      iii) when an embryo having an orientation matching a predetermined orientation is detected by the orientation detector (10), the flow direction means (18) is controlled such that the flow of the liquid in the flow channels is directed from the inlet (1) to the outlet (3);
      iii) when an embryo having an orientation opposite to the predetermined orientation is detected by the orientation detector (10), the flow direction means (18) is controlled such that the flow of the liquid in the flow channels is directed from the inlet (1) toward the reservoir device (6) so that the embryo enters the reservoir tube (5), after which the flow direction means (18) is controlled such that the flow of the liquid in the flow channels is directed from the reservoir device (6) to the outlet (3) so that the embryo enters the outlet tube (4), after which the flow direction means (18) is controlled such that the flow of the liquid in the flow channels is directed from the inlet (1) to the outlet (3);
whereby all embryos suspended in the liquid exiting from the outlet (3) will have an orientation matching the predetermined orientation.

Apparatus additionally capable of sorting acceptable embryos from other objects is also disclosed comprising:
   a) flow direction means (18) additionally comprise means of directing the flow into either an embryo receiver (20) or a secondary destination (21);
   b) the orientation detector (10) additionally comprises means of separating acceptable embryo from other objects;
   c) control unit (17) comprises additional means of controlling the flow direction means (18) such that:
      i) in a default position, when no object is detected by the orientation detector (10), the flow direction means (18) is controlled such that the flow of the liquid in the flow channels is directed from the inlet (1) to the outlet (3) and the outlet flow is directed into the secondary destination (21);
      ii) when an object other than an acceptable embryo is detected by the orientation detector (10), the flow direction means (18) is controlled such that the flow of the liquid in the flow channels is directed from the inlet (1) to the outlet (3) and the outlet flow is directed into the secondary destination (21);
      iii) when an acceptable embryo having an orientation matching a predetermined orientation is detected by the orientation detector (10), the flow direction means (18) is controlled such that the flow of the liquid in the flow channels is directed from the inlet (1) to the outlet (3) and the outlet flow is directed into the embryo receiver (20);

iv) when an acceptable embryo having an orientation opposite to the predetermined orientation is detected by the orientation detector (10), the flow direction means (18) is controlled such that the flow of the liquid in the flow channels is directed from the inlet (1) to the reservoir device (6) so that the embryo enters the reservoir tube (5), after which the flow direction means (18) is controlled such that the flow of the liquid in the flow channels is directed from the reservoir device (6) to the outlet (3) so that the embryo enters the outlet tube (4), after which the flow direction means (18) is controlled such that the flow of the liquid in the flow channels is directed from the inlet (1) to the outlet (3) and the outlet flow is directed into the embryo receiver (20);

whereby all acceptable embryos suspended in the liquid exiting from the outlet (3) will be directed into the embryo receiver (20) and will have an orientation matching the predetermined orientation and whereby other objects are sorted into the secondary destination (21).

The apparatus may more specifically be characterised by that:

a) the flow direction means comprise an inletg valve (8) placed in the inlet tube (2) and outlet valve (9) placed in the outlet tube (4), wherein said valves provide means of controlling the flow in the flow channels by opening and closing in response to control signals;

b) the control unit (17) comprises means of controlling the valves (8) and (9) such that:
  i) in a default position, when no embryo is detected by the orientation detector (10), the inlet valve (8) is open and the outlet valve (9) is open, whereby the flow of the liquid in the flow channels is directed from inlet (1) to outlet (3);
  ii) when an embryo having an orientation matching a predetermined orientation is detected by the orientation detector (10), the inlet valve (8) remains open and the outlet valve (9) remains open, whereby the flow of the liquid in the flow channels remains directed from inlet (1) to outlet (3); and
  iii) when an embryo having an orientation opposite to the predetermined orientation is detected by the orientation detector (10), the inlet valve (8) remains open and the outlet valve (9) is closed, whereby the flow of the liquid in the flow channels is directed from inlet (1) to the reservoir device (6) so that the embryo enters the reservoir tube (5), after which the inlet valve (8) is closed and the outlet valve (9) is opened whereby the flow of the liquid in the flow channels is directed from the reservoir (6) to outlet (3) so that the embryo to enters the outlet tube (4), after which the inlet valve (8) is opened and the outlet valve (9) remains open, whereby the flow of the liquid in the flow channels is again directed from inlet (1) to outlet (3) as in the default position;

whereby all embryos suspended in the liquid exiting from the outlet (3) will have an orientation matching the predetermined orientation.

The apparatus may more specifically comprise one or more of the following:

(a) an additional reservoir tube detector (11) comprising means of detecting the presence or absence of an embryo in reservoir tube (5), in which case the control unit (17) comprises means of receiving input from the reservoir tube detector (11) to determine when an embryo has entered the reservoir tube (5) by waiting for the reservoir tube detector (11) to detect the presence and the location of an embryo in the reservoir tube (5); and/or (b) an additional outlet tube detector (12) comprising means of detecting the presence or absence of an embryo in the outlet tube (4), in which case the control unit (17) comprises means of receiving input from the outlet tube detector (12) to determine when an embryo has entered the outlet tube (4) by waiting for the outlet tube detector (12) to detect the presence and location of an embryo in the outlet tube (4); and/or One or more cases when an object or an embryo is to enter a particular location may be determined by a predetermined timing based on a constant flow rate of the liquid flowing though the apparatus.

The reservoir device (6) may comprise a liquid container open to atmospheric pressure containing liquid having a surface level higher relative to the outlet (3) such that the hydrostatic pressure is sufficient to provide liquid flow in the flow channels from the reservoir device (6) to outlet (3) when the flow direction means are set accordingly.

The reservoir device (6) may preferably have a much larger horizontal cross-sectional area compared to the cross-sectional area of the reservoir tube (5), such that the level of liquid inside reservoir (6) is substantially constant during operation.

The valves (8) and/or (9) may be solenoid pinch valves.

The orientation detector (10) preferably comprises a digital imaging means and computerized image analysis means.

A computer program product for use in an apparatus according to the above is disclosed, comprising computer readable code means, which when run in a control unit (17) of the apparatus causes the control unit (17) to perform the action described above associated with the control unit (17) in response to the inputs to the control unit (17) described above.

A second computer program product for detecting the orientation of individual embryos and optionally also the acceptability of an embryo in an apparatus according to the above is disclosed, comprising computer readable code means, which when run in an orientation detector (10) of the apparatus causes the orientation detector (10) to perform the steps of
 i) image acquisition;
 ii) image analysis;
 iii) detecting the orientation of an embryo; and
 iv) optionally, determining the acceptability of an embryo.

The step of detecting the orientation of an embryo may further comprise one or more of the steps of:
 i) examining the thickness of the embryo at both ends and the middle, whereby the side with the larger thickness is deemed to be the crown; and/or
 ii) examining the edge of the embryo to find the side with the crown, wherein the side with more edges is deemed to be the crown.

The step of detecting the acceptability of an embryo may further comprise the steps of:
 i) examining the size of the embryo;
 ii) examining the thickness of the embryo at both ends and the middle, whereby the side with the larger thickness is deemed to be the crown; and
 iii) examining the edge of the embryos to find the side with the crown, wherein the side with more edges is deemed to be the crown;

whereby embryos having size smaller than a threshold value, embryos having larger thickness at the middle than at both ends, and embryos giving conflicting results from the steps (ii) and (iii) as to the direction of the crown are deemed not acceptable.

The invention provides at least the following advantages:
Planting the embryo in the correct orientation
Low cost
Accurate orienting, and facilitating sorting of viable embryos from other objects
Imaging and characterization of each somatic embryo is made possible
Fast processing of large numbers of embryos
Gentle handling of somatic embryos in liquid phase increases conversion rate of mature embryos to germinated embryos
Efficient apparatus allows for sufficient yield of mature embryos also from cell lines that are only producing limited numbers of mature embryos

DEFINITIONS

The terms somatic embryo and somatic plant embryo are used interchangeably. The terms refer to plant embryos derived from somatic tissue of a plant.

Cotyledon a part of a plant embryo (100) that becomes the embryonic first leaves of a seedling. The cotyledon is located at one end of a plant embryo opposite to the end where roots will eventually form (foot (102)). When there are several cotyledons, the may form a structure referred to as a crown (101).

Diameter of the crown refers to the diameter of a crown structure at its widest (103).

Length of a plant embryo refers to the linear distance from the tip of the root end to the tip of the cotyledon end measured along the longitudinal axis of the embryo (104).

Norway spruce is a spruce species with the Latin name *Picea abies* native to Europe.

The terms tube, channel and flow channel are used interchangeably. The terms are used without specific reference to any particular geometric shape of the cross-section, unless specifically stated otherwise.

a) An apparatus of the invention with two valves as flow direction means. The reservoir device illustrated is a tank open to atmosphere.

b) Detail of an apparatus of the invention having a three-way valve as flow direction means between reservoir tube and outlet tube.

c) An illustration of a three-way valve useful as flow direction means for an apparatus of the invention.

d) Detail of an apparatus of the invention with a single embryo receiver.

e) Detail of an apparatus of the invention with multiple embryo receivers.

f) Detail of an apparatus of the invention with a three-way valve attached to the outlet tube as a part of the flow direction means.

Figure 3:
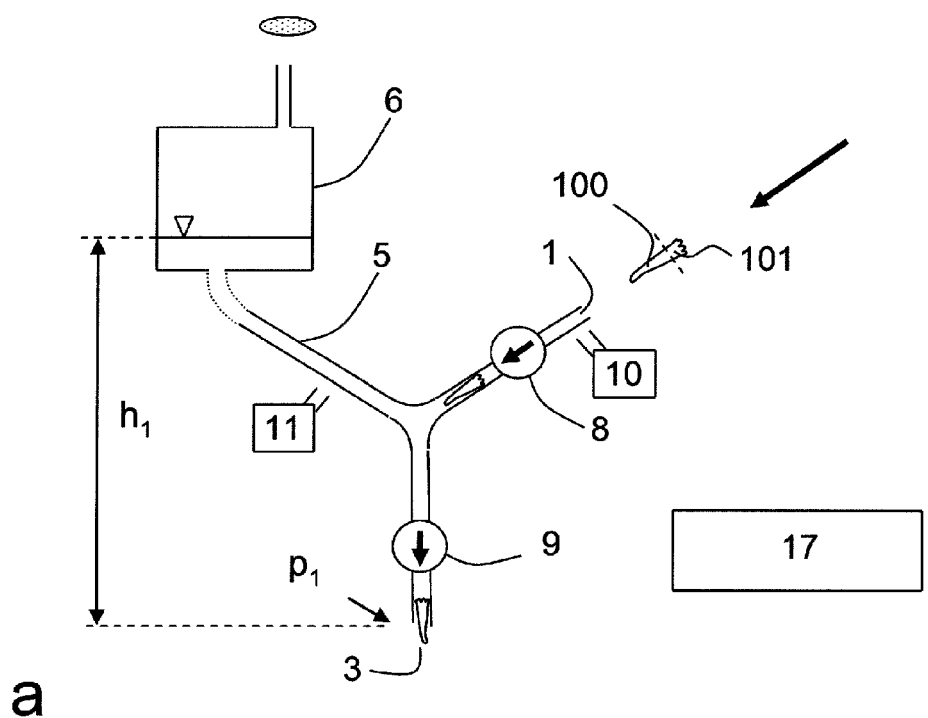
Figure 3:
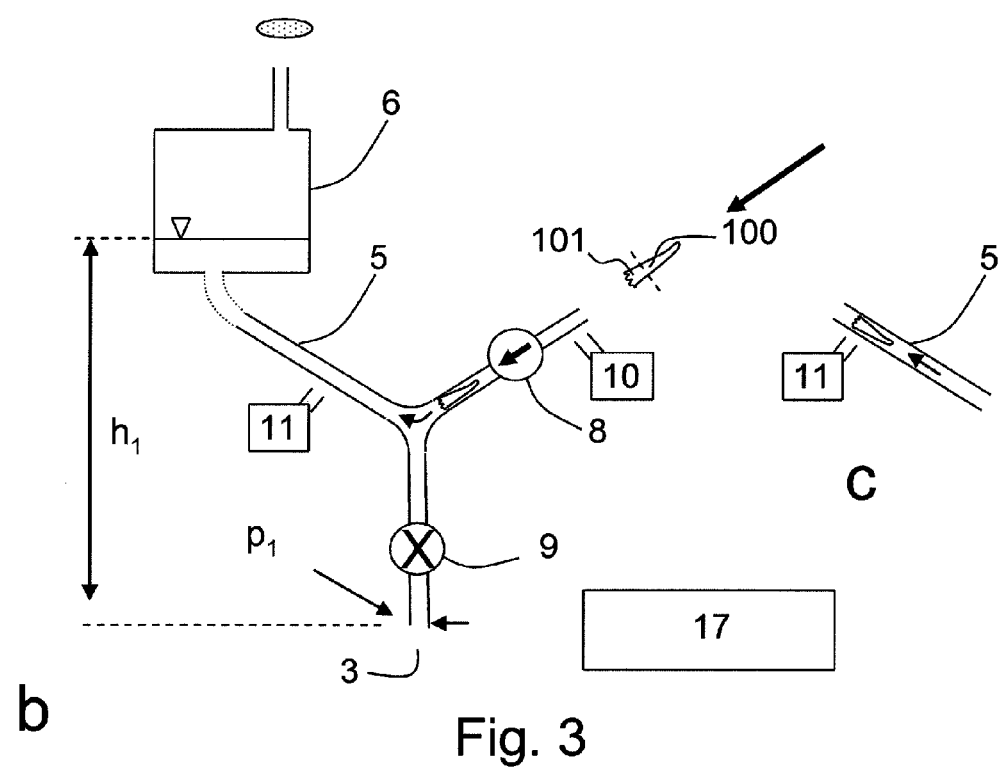
Figure 3:
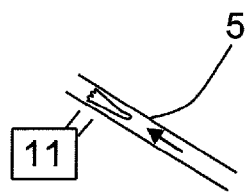
Figure 3:
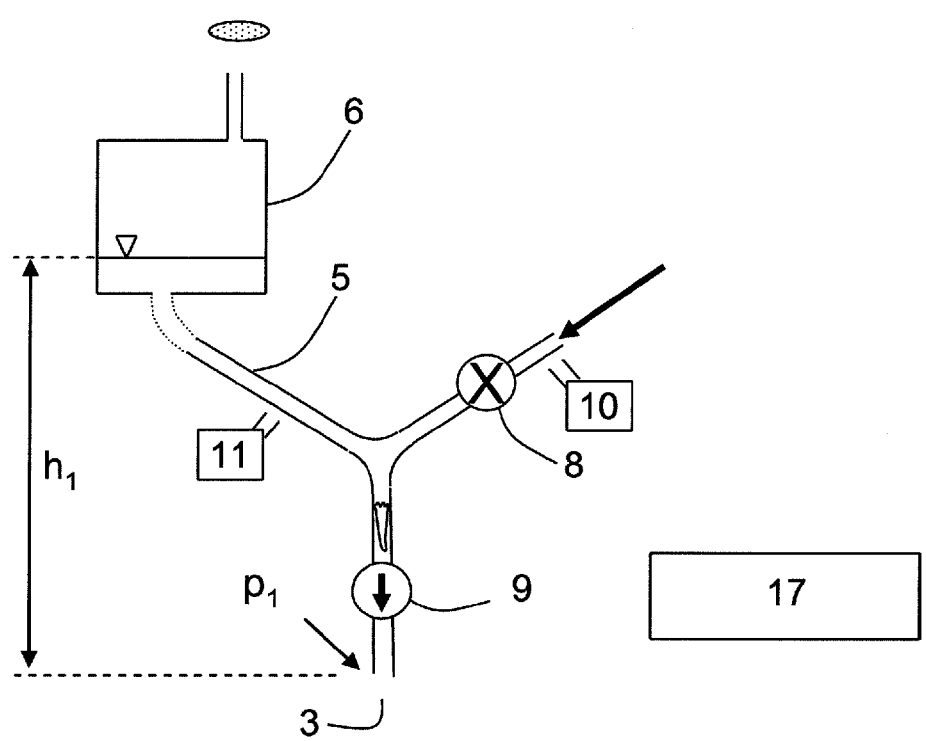

FIG. 3 illustrates the function of an apparatus of the invention. An X denotes a closed valve, and the arrows denote the direction of the flow in an open valve.

a) Illustrates the case when an embryo having an orientation matching a predetermined orientation (here: crown-last) is detected by the orientation detector (10), the inlet valve (8) remains open and the outlet valve (9) remains open, whereby the flow of the liquid in the flow channels remains directed from inlet (1) to outlet (3)

b) Illustrates the case when an embryo having an orientation opposite to the predetermined orientation is detected by the orientation detector (10), the inlet valve (8) remains open and the outlet valve (9) is closed, whereby the flow of the liquid in the flow channels is directed from inlet (1) to the reservoir device (6) so that the embryo enters the reservoir tube (5)

c) The embryo may flow up the reservoir tube, until its presence in the reservoir tube (5) is detected by the optional reservoir detector (11)

d) After the embryo has entered the reservoir tube, the inlet valve (8) is closed and the outlet valve (9) is opened whereby the flow of the liquid in the flow channels is directed from the reservoir device (6) to outlet (3) so that the embryo enters the outlet tube (4), after which the inlet valve (8) is opened and the outlet valve (9) remains open, whereby the flow of the liquid in the flow channels is again directed from inlet (1) to outlet (3) as in the default position;

DETAILED DESCRIPTION OF THE INVENTION

Effective planting of plant embryos requires that they are oriented correctly, i.e. that the root is planted downwards. An apparatus for automated orienting plant embryos is disclosed. The apparatus operates on individual plant embryos suspended (in random orientation) in a liquid flowing though the apparatus. The liquid may be any liquid which is not too viscous for flow in the apparatus, and which is benign to the embryos, such as water. Below, reference is made to the components listed in table 2.

TABLE 2

Orientation/sorting device component list

| Item | Designation |
| --- | --- |
| 1 | Liquid inlet |
| 2 | Inlet tube |
| 3 | Liquid outlet |
| 4 | Outlet tube |
| 5 | Reservoir tube |
| 6 | Reservoir device |
| 7 | Intersection |
| 8 | Inlet valve (optional) |
| 9 | Outlet valve (optional) |
| 10 | Orientation detector |
| 11 | Reservoir tube detector (optional) |
| 12 | Outlet tube detector (optional) |
| 17 | Control unit |
| 18 | Flow Direction means |
| 19 | Three-way intersection valve (optional) |
| 20 | Embryo receiver (optional) |
| 21 | Secondary destination (optional) |
| 22 | Secondary outlet tube (optional) |
| 23 | Secondary intersection (optional) |
| 24 | Liquid drainage (optional) |
| 30 | Inlet/outlet openings of the intersection valve |
| 31 | Intersection valve house |
| 32 | Intersection valve rotor |
| 33 | Intersection valve rotor flow channel |
| 34 | Diameter of inlet/outlet |
| 40 | x, y-movable table device (optional) |
| 41 | Device for x, y-moving the outlet tube (4) (optional) |
| 50 | Three way valve at secondary intersection (23) (optional) |
| 60 | Tube air inlet/outlet to reservoir device (optional) |
| 61 | Air inlet/outlet (optional) |
| 62 | Air filter (optional) |

Overall Construction

Figure 1:
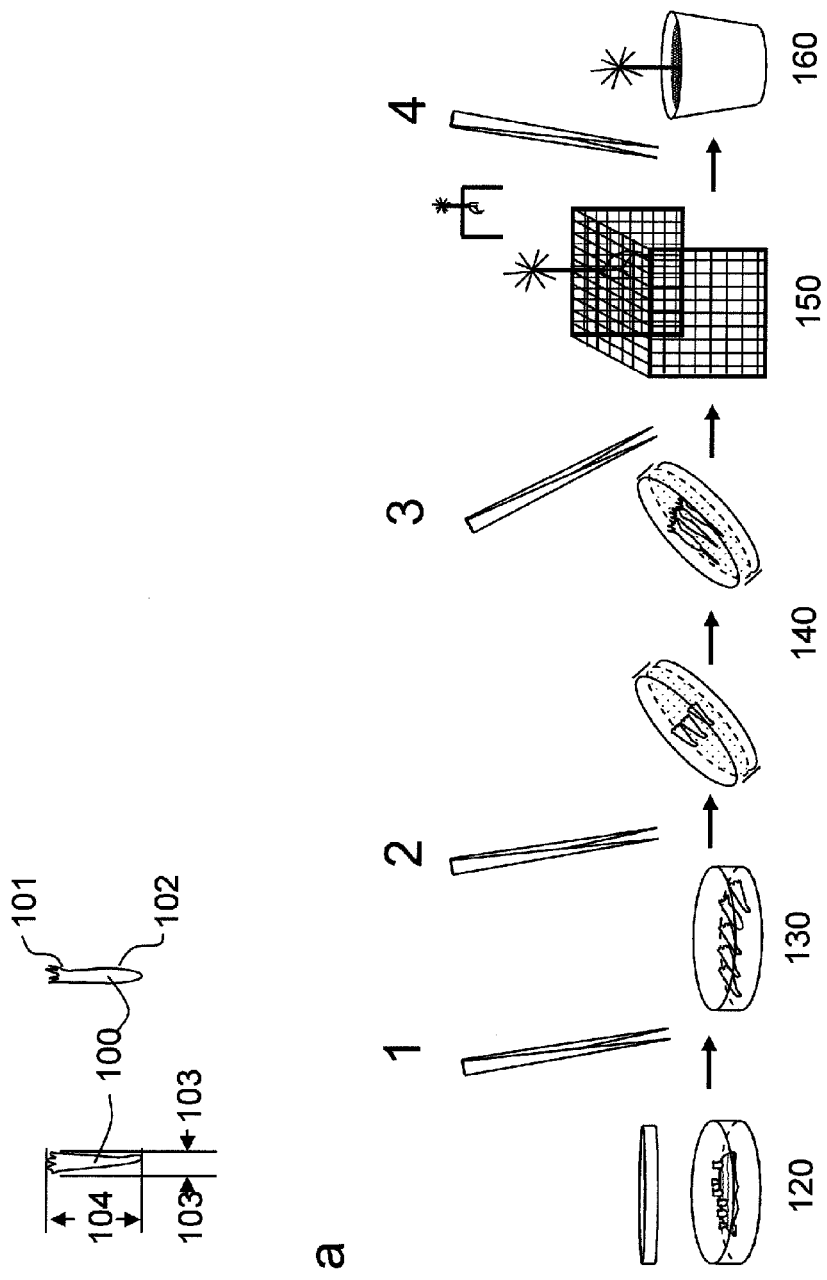
FIG. 1 illustrates a general process of producing somatic plant embryos.
Figure 2:
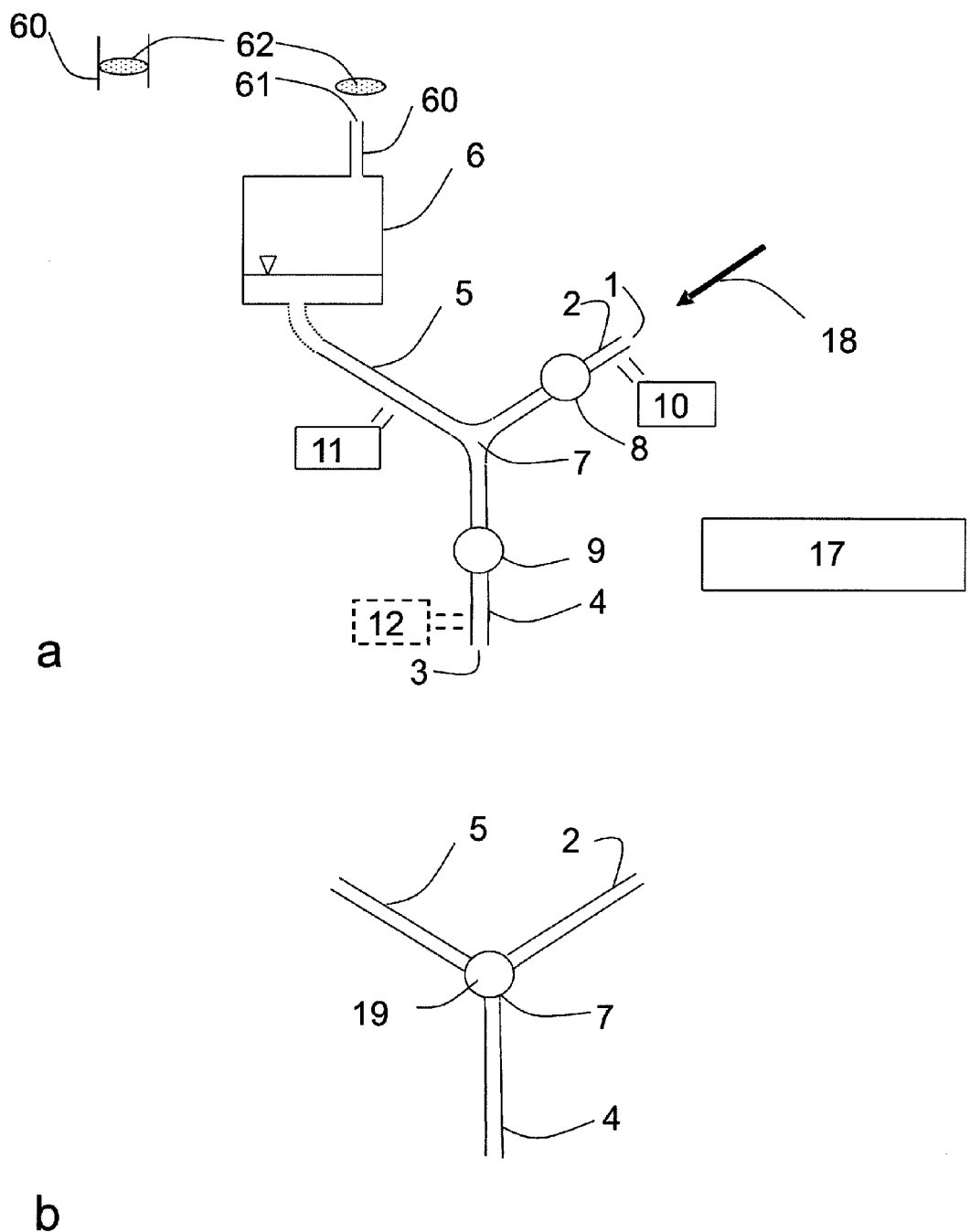
FIG. 2 illustrates the construction of certain details of an apparatus of the invention.
Figure 2:
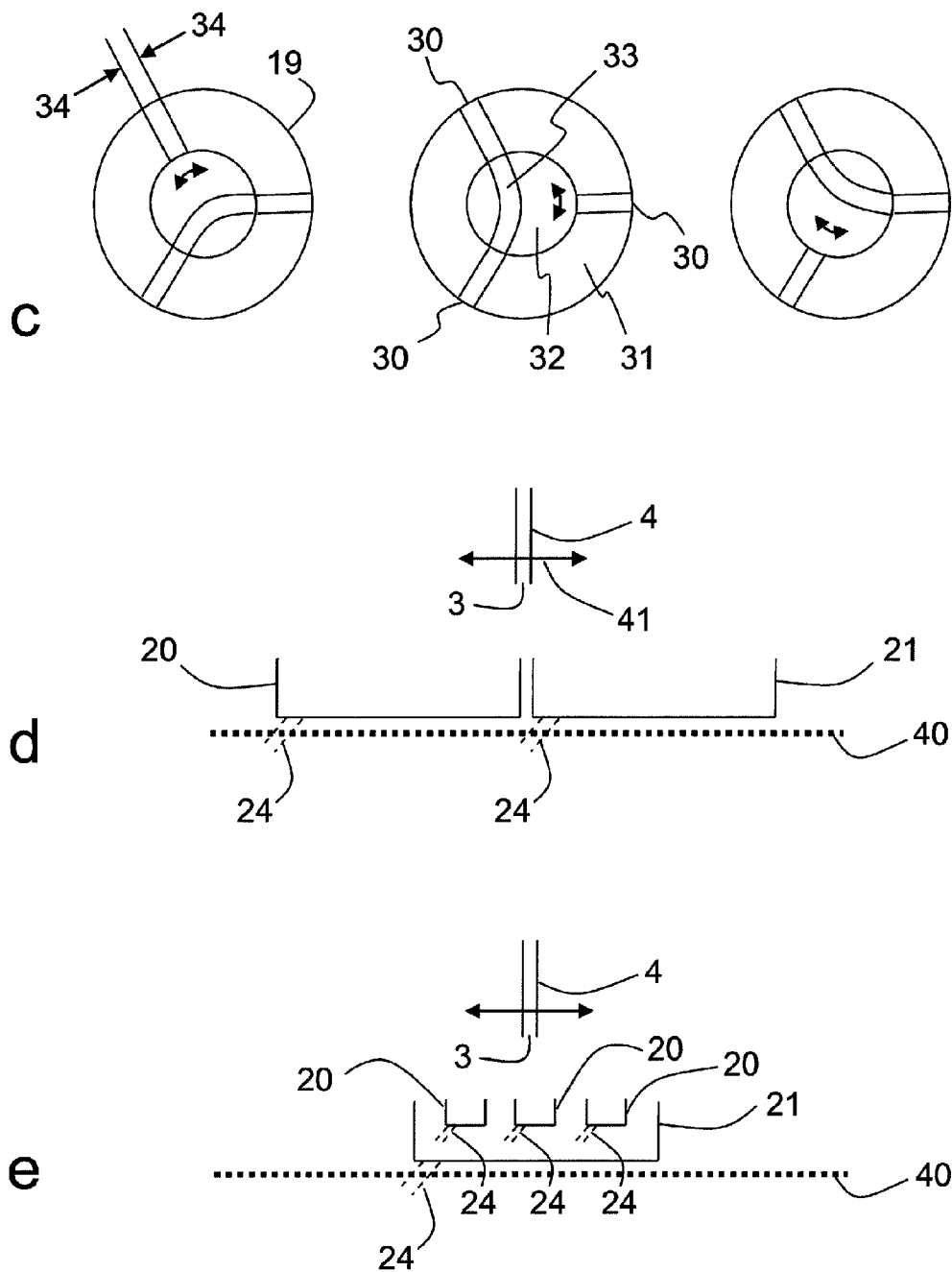
Figure 2:
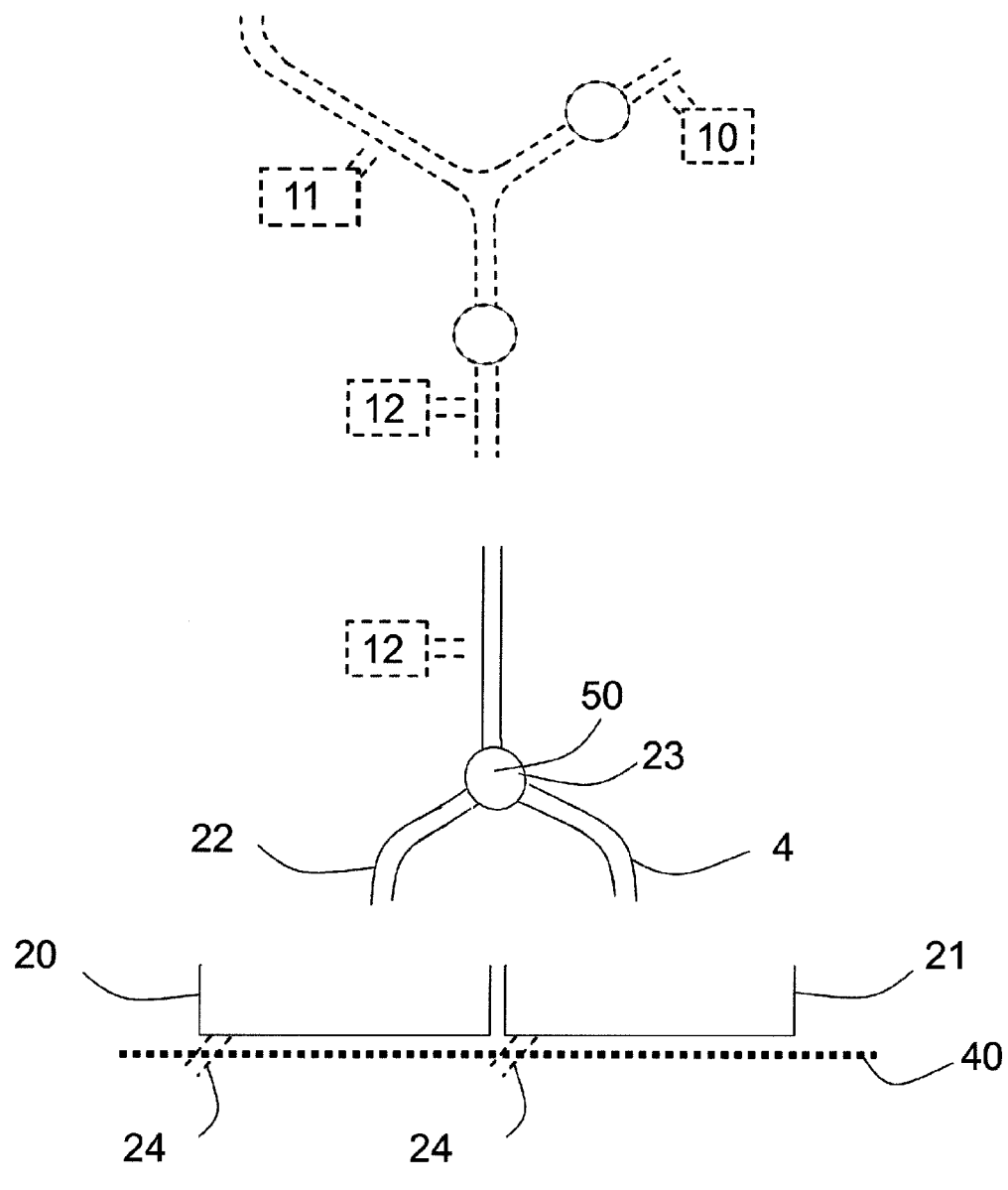

The overall construction of the orientation apparatus is presented in FIG. 2. The apparatus comprises flow channels for the liquid comprising liquid inlet (1) of an inlet tube (2), liquid outlet (3) of an outlet tube (4) and reservoir tube (5) connected to a reservoir device (6). All tubes are connected at an intersection (7). The contact angles between tubes (2), (4) and (5) at the intersection (7) should not be too narrow as this will subject the plant embryos to increased undesirable bending stress. The intersection (7) is preferably planar and all the three tubes meet at 120° angles relative to each other, to minimize bending forces acting on the embryos. Optionally, the liquid outlet (3) flow may be controllable into an embryo receiver (20) or to a secondary destination (21).

Dimensions of the Flow Channels

The flow channels are dimensioned such that the embryos may travel with the liquid flowing though the channels but are restricted to travelling either in a crown-first or crown-last orientation by dimensional constraints. Preferably, the flow channels have an essentially circular or oval cross-section, although other geometries may be used as long as the embryos are not damaged during their passage through the flow channels. Flow channels with essentially circular or oval cross-section are easier to manufacture than flow channels with other geometries and provide the minimum of stress to the embryos. Also preferably, the flow channels are smooth on the inside. Any roughness on the inner surfaces may easily damage the delicate embryos and is thus best avoided. The largest internal cross-sectional dimension of the flow channels is preferably no larger than about 95% of the length of the embryos to be sorted. The smallest internal cross-sectional dimension of the flow channels is at least 100% of the crown diameter of the embryos to be sorted. For Norway spruce embryos as an example, the diameter of an essentially circular flow channel is preferably about 2.95 mm.

Flow Direction Means

The apparatus comprises flow direction means (18) (see FIGS. 2 and 3) having means of
i) directing the flow from the inlet (1) to the outlet (3);
ii) directing the flow from the inlet (1) toward the reservoir device (6);
iii) directing the flow from the reservoir device (6) to the outlet (3);
iv) optionally, means of directing the outlet (3) flow to an embryo receiver (20) or to a secondary destination (21)

Any means of controllably regulating and/or directing liquid flow that do not subject the embryos to too damaging amounts of stress may potentially be used as flow direction means.

The flow direction means may comprise an inlet valve (8) placed in the inlet tube (2) and outlet valve (9) placed in the outlet tube (4), wherein said valves provide means of controlling the flow in the flow channels by opening and closing in response to remote control signals. The valves (8) and (9) are preferably solenoid pinch valves, with the relevant tube sections at the valves being flexible. This arrangement has the advantage of the valves not being in direct contact with the liquid and the system thus being easy to sterilize and maintain.

Alternatively, the flow direction means may comprise three-way valves well known in the art and illustrated in FIG. 2c, or similar known devices for directing the flow of a liquid. For example, the flow direction means may comprise a three-way intersection valve (19) located at the intersection (7) as illustrated in FIG. 2c.

The means of directing outlet (3) flow to the embryo receiver (20) or a secondary destination (21) may comprise controllable means of relocating the embryo receiver (20) in relation to the outlet (3) such that the outlet (3) flow brings the embryos to the receiver (20) or such that the flow is directed to a secondary destination (21). Alternatively, the desired effect may be achieved with controllable means of relocating the outlet (3) in relation to the embryo receiver (20) and the secondary destination (21). Certain exemplary configurations are illustrated in FIGS. 2d and 2e (the arrows illustrating movement). The embryo receiver (20) may comprise a plurality of individual embryo receivers such as wells in a microtiter plate, discrete planting substrate containers ordered into a plate having several rows and columns or a string of discrete planting substrate containers coupled together. Means of relocating referred to above may for example comprise x/y means or linear means, such as electromagnetic, motor driven, pneumatic or hydraulic actuators preferably remote-controlled by the control unit (17). One specific example is a x/y-drivable table steered by the control unit (17). In a configuration having a plurality of individual embryo receivers the means of relocating the embryo receiver (20) may preferably comprise x/y-capable means of relocation. Alternatively, if a string of discrete planting substrate containers coupled together is used, a linear means of relocation may be preferable.

Alternatively, an optional secondary outlet tube (22) leading to the secondary destination (21), connected to the outlet tube (4) at a secondary intersection (23) could be used to achieve the flow direction between the embryo receiver (20) and a secondary destination (21). In a configuration comprising a secondary outlet tube (22), the flow direction means may comprise controllable valves placed in the secondary outlet tube (22) and the outlet tube (4) downstream of the secondary intersection (23). The controllable valve could comprise solenoid pinch valves, which can be used to controllably and selectively close the part of the flow path to which the flow is not to be directed.

The same effect could alternatively be achieved using a three-way valve (50) placed in the secondary intersection (23). Yet another alternative means for implementing flow direction could comprise a fluid stream switching device such as disclosed in US2002192040A cited above placed in the secondary intersection (23).

The embryo receivers (20) and/or the secondary destinations (21) may be equipped with liquid drainages (24), which may comprise hole, grits, tubes, channels or other means of draining the liquid.

Multiple other possible solutions for implementing the flow direction means would be apparent to the skilled person.

Reservoir Device

The reservoir device (6) comprises means for maintaining a higher liquid pressure or head in relation to the liquid pressure at outlet (3), means for accommodating liquid flowing in as well as means of providing liquid for outward flow.

The reservoir device (6) preferably comprises a relatively large liquid container with surface area of the liquid in the liquid container being many times larger than the cross-sectional surface area of tube (5), and the reservoir (6) being open to atmospheric pressure containing liquid having a surface level higher relative to the outlet (3) such that the hydrostatic pressure is sufficient to provide liquid flow in the flow channels from the reservoir device (6) to outlet (3) when the flow direction means are set accordingly. In such embodiment, the reservoir device (6) is partially filled with the liquid during operation. Thus, when the flow is directed to the reservoir device (6), the liquid may be accommodated with the result that the liquid level will rise, but will rise only slightly because of the large surface area of the liquid in the reservoir device (6), and therefore, the hydrostatic pressure head will change, but will change only slightly. When the flow is directed from the reservoir device (6) into the tube (5), liquid may be dispensed with the result that the liquid level will drop in the reservoir device (6), but will drop only slightly. The reservoir device (6) (as shown in FIG. 2) may be air tight except for an inlet (60) which is open to atmospheric pressure via a tube (61) having a filter (62). The filter (62) is preferably a sterile filter having such small pore size that microorganisms cannot pass the filter, preferably less than 0.22 μm. When the flow enters or leaves the reservoir and consequently the liquid level rises or drops in the reservoir, the air in the reservoir can only leave and enter back into the reservoir only through the tube (61) and the filter (62) keeping the air and the liquid in the reservoir sterile.

A sufficiently long elongation of the reservoir tube (5) placed suitably in relation to the outlet (3) could be used as a reservoir device (6) but would have the disadvantages of more variable head. The variability of the head could be reduced by using a pump, such as a peristaltic pump or a piston pump to generate the required pressure. The reservoir device (6) may be a container made out of elastic material wherein the elasticity of the material provides the functions of accommodating liquid when the container expands and generating sustained pressure for outward flow as the container recoils. In yet another alternative, the reservoir device (6) may be a container comprising a movable element to adjust the volume of the container. The movable element provides back pressure by means such as a spring, a magnetic device or a motor. A container where controlled inflow of pressurized gas (preferably inert gas) provides pressure for outward flow, and release of gas from the container provides headroom in the situation where accommodation of inflowing liquid is required could be used as a reservoir device. In summary, there are many alternative implementations of the reservoir device (6) within reach of the skilled person.

Detectors

In order to follow the movement of the embryos and optionally other objects, the apparatus comprises one or more detectors.

The apparatus comprises an orientation detector (10) placed in the inlet tube (2), wherein the orientation detector (10) comprises means of determining the orientation of an embryo passing though the inlet tube (2). The orientation detector (10) may additionally comprise means of separating acceptable embryo from other objects. The orientation detector (10) may be placed anywhere in the inlet tube (2) upstream of the intersection (7). The orientation detector (10) as referred to here encompasses any one or a combination of any sensor, optical or otherwise, or a machine vision system, or an image analysis system, or any other means of determining the orientation of the embryo.

The apparatus may comprise one or more of the following: an additional reservoir tube detector (11) comprising means of detecting the presence and the location of an embryo in the reservoir tube (5), and/or an additional outlet tube detector (12) comprising means of detecting the presence and the location of an embryo in the outlet tube (4).

The orientation detector (10) comprises an optical imaging means and image analysis means. The optical imaging means may comprise a digital camera. The orientation detector (10) has computational and storage capabilities, and can be provided as one physical unit, or alternatively as a plurality of logically interconnected units. The image analysis means may be implemented in a unit that is physically the same as the control unit (17) or in a physically separate unit. The image analysis means may be implemented by means of a computer program, see a separate section below.

The orientation detector (10) may comprise a laser-based optical sensor for detecting the presence of an object in the detection line of the sensor in addition and in combination to a digital camera and image analysis means, as well as means of triggering the digital camera in response to a detected object. The optical imaging means may further comprise a light source such as a flash, optionally under the control of said additional laser-based optical sensor.

The detectors (11) and (12) may comprise photo sensors. Photo sensors for use with the invention may be in principle any of the many photo sensors known in the art suitable for the purpose. Examples of suitable detectors (11) and (12) include but are not limited to those based on one or more optical beam(s) including laser beam(s), induction sensors, sonic sensors including ultrasonic sensors.

The flow channels need to be sufficiently transparent for the wavelengths utilized by the photo sensors or imaging means used, at least at the locations where these devices are placed. This may be achieved for example by manufacturing the flow channels of a transparent material such as glass, or by placing windows in the flow channels at desired locations.

Control unit Functions

Depending on input from the orientation detector (10) and optional detectors such as (11) and/or (12), the flow direction means are controlled by a control unit (17).

The apparatus comprises a control unit (17) for steering the flow of the liquid in the flow channels comprises means of receiving input from the orientation detector (10) and means of controlling the flow direction means (18) such that:

i) in a default position, when no embryo is detected by the orientation detector (10), the flow direction means (18) is controlled such that the flow of the liquid in the flow channels is directed from the inlet (1) to the outlet (3);

ii) when an embryo having an orientation matching a predetermined orientation is detected by the orientation detector (10), the flow direction means (18) is controlled such that the flow of the liquid in the flow channels is directed from the inlet (1) to the outlet (3); and iii) when a embryo having an orientation opposite to the predetermined orientation is detected by the orientation detector (10), the flow direction means (18) is controlled such that the flow of the liquid in the flow channels is directed from the inlet (1) to the reservoir device (6) so that the embryo enters the reservoir tube (5), after which the flow direction means (18) is controlled such that the flow of the liquid in the flow channels is directed from the reservoir device (6) to the outlet (3) so that the embryo enters the outlet tube (4), after which the flow direction means (18) is controlled such that the flow of the liquid in the flow channels is directed from the inlet (1) to the outlet (3).

As a result of the operation disclosed above, all embryos suspended in the liquid exiting from the outlet (3) will have an orientation matching the predetermined orientation.

The control unit (17) may additionally comprise means of controlling the flow direction means (18) such that:

v) in a default position, when no object is detected by the orientation detector (10), the flow direction means (18) is controlled such that the flow of the liquid in the flow channels is directed from the inlet (1) to the outlet (3) and the outlet flow is directed into the secondary destination (21);

vi) when an object other than an acceptable embryo is detected by the orientation detector (10), the flow direction means (18) is controlled such that the flow of the liquid in the flow channels is directed from the inlet (1) to the outlet (3) and the outlet flow is directed into the secondary destination (21);

vii) when an acceptable embryo having an orientation matching a predetermined orientation is detected by the orientation detector (10), the flow direction means (18) is controlled such that the flow of the liquid in the flow channels is directed from the inlet (1) to the outlet (3) and the outlet flow is directed into the embryo receiver (20);

viii) when an acceptable embryo having an orientation opposite to the predetermined orientation is detected by the orientation detector (10), the flow direction means (18) is controlled such that the flow of the liquid in the flow channels is directed from the inlet (1) to the reservoir device (6) so that the embryo enters the reservoir tube (5), after which the flow direction means (18) is controlled such that the flow of the liquid in the flow channels is directed from the reservoir device (6) to the outlet (3) so that the embryo enters the outlet tube (4), after which the flow direction means (18) is controlled such that the flow of the liquid in the flow channels is directed from the inlet (1) to the outlet (3) and the outlet flow is directed into the embryo receiver (20);

As a result of the operation disclosed above, all acceptable embryos suspended in the liquid exiting from the outlet (3) will be directed into the embryo receiver (20) and will have an orientation matching the predetermined orientation and whereby other objects that are not considered as acceptable embryos are sorted into the secondary destination (21).

When the apparatus comprises valves (8) and (9) (see FIGS. 3a and 3b), the control unit (17) may comprise means of controlling to the valves (8) and (9) such that:

i) in a default position, when no embryo is detected by the orientation detector (10), the inlet valve (8) is open and the outlet valve (9) is open, whereby the flow of the liquid in the flow channels is directed from inlet (1) to outlet (3);

ii) when an embryo having an orientation matching a predetermined orientation is detected by the orientation detector (10), the inlet valve (8) remains open and the outlet valve (9) remains open, whereby the flow of the liquid in the flow channels remains directed from inlet (1) to outlet (3); and iii) when an embryo having an orientation opposite to the predetermined orientation is detected by the orientation detector (10), the inlet valve (8) remains open and the outlet valve (9) is closed, whereby the flow of the liquid in the flow channels is directed from inlet (1) to the reservoir device (6) so that the embryo enters the reservoir tube (5), after which the inlet valve (8) is closed and the outlet valve (9) is opened whereby the flow of the liquid in the flow channels is directed from the reservoir (6) to outlet (3) so that the embryo enters the outlet tube (4), after which the inlet valve (8) is opened and the outlet valve (9) remains open, whereby the flow of the liquid in the flow channels is again directed from inlet (1) to outlet (3) as in the default position.

As a result of the operation disclosed above, all embryos suspended in the liquid exiting from the outlet (3) will have an orientation matching the predetermined orientation.

The embryo preferably does not enter the reservoir device (6) in the operations above. When the reservoir device (6) comprises a relatively large liquid quantity as described above, the embryo should not be allowed to enter the reservoir device (6) at all as the orientation of the embryo would become randomized.

One or more cases when an object or an embryo is to enter or has entered a particular location may be determined by a predetermined timing based on a constant flow rate of the liquid flowing though the apparatus. However, considering that the precise speed of the embryo inside the tube depends on the precise size and the shape of the embryo, preferably at least detector (11) is utilized to pinpoint the location of the embryo while in tube (5). To achieve even more precise control over the timing of the deposition of an acceptable embryo in embryo receiver (20), the apparatus may also comprise a detector (12) for detecting the location of the embryo.

Control Unit

The control unit (17) has computational and storage capabilities, and can be provided as one physical unit, or alternatively as a plurality of logically interconnected units. The control unit (17) may be implemented in many ways. For instance, the control unit (17) could be an ordinary commercially available personal computer or a specifically tailored microprocessor-controlled control unit.

Means of controlling other units and receiving input from other units can be implemented in many ways, wired and wireless. For instance, the control unit may comprise a D/A converter input-output unit capable of producing analogue electric signals that can be transmitted through wires. The signals sent by the control unit (17) could be digital such as via serial port, parallel port, USB port, Firewire (IEEE1394) or similar wired signals. Alternatively, the signals could be wireless though acoustic, optical, infrared or radiofrequency signals. For example, the Bluetooth or wireless LAN technologies could be used to transmit the signals from the control unit (17) to the flow direction means (18).

Computer Program Product for Controlling the Apparatus

It should be noted that the control unit (17) comprises logic for performing the functionality of the orientation apparatus. This functionality may be implemented by means of a software or computer program. The control unit (17) may also comprise storage means or a memory unit for storing the computer program and processing means or a processing unit, such as a microprocessor, for executing the computer program. The storage means may also be readable storage medium separated from, but connected to the control unit (17). When, in the above, it is described that the orientation apparatus performs a certain function it is to be understood that the control unit (17) in the orientation apparatus uses the processing means to execute a certain part of the program which is stored in the storage means.

The invention relates also to a computer program product which, when run in a control unit (17), causes the control unit (17) to perform the actions described above in response to the inputs described above.

Computer Program Product for Analyzing Orientation and Acceptability of Embryos

The image analysis means functionality of the orientation detector (10) may be implemented by means of a software or computer program.

The orientation detector (10) may also comprise storage means or a memory unit for storing the computer program and processing means or a processing unit, such as a microprocessor, for executing the computer program. The storage means may also be readable storage medium separated from, but connected to the orientation detector (10) When, in the above, it is described that the orientation apparatus performs a certain function it is to be understood that the orientation detector (10) in the orientation apparatus uses the processing means to execute a certain part of the program which is stored in the storage means. Preferably, the same physical unit that provides the control unit (17) functionality also provides the image analysis functionality as this allows for a simpler construction and requires less communication between physical units.

The background of the image to be analyzed may be removed by subtracting a previously captured background image, leaving only the difference between the two images, which simplifies and speeds up the computational analysis. The intensity plane may then be extracted, effectively converting the image to pure grayscale (if the image was acquired in color), to further improve computational speed. From the known top and bottom boundaries of the tube a region of interest (ROI) within the image may be defined which yet further reduces the computational load.

Embryos being smaller that a threshold value (e.g. 3 mm for Norway Spruce) in length as well as those embryos that do not have proper shape and aspect ratio may be rejected. The size threshold value may vary from plant species to plant species. An embryo having midsection that is thicker than both ends may be rejected. The embryos that have proper shape may be examined to determine their orientation. If the orientation matches the desired orientation, the embryo is allowed to pass on without action. If the orientation does not match the desired orientation, then the embryo is directed to go through the reorientation procedure as described above prior to proceeding.

The detection of the embryo orientation and acceptability may be based on two tests, aspect ratio (test A) and edge detection (test B), as outlined below Test A: Examines the thickness of the embryo at both ends and the middle, whereby the side with the larger thickness is deemed to be the crown. If the midsection is found to be thicker than both ends, then the embryo is rejected.

Test B: Examines the edge of the embryo to find the side with the crown, wherein the side with more edges is deemed to be the crown.

If both tests A and B agree, the program may assign a definite orientation and send output to the control unit (17) which directs the flow direction means (18) accordingly to either reorient the embryo or not. If tests A and B do not agree, the embryo may be rejected and the control unit (17) directs the flow direction means (18) accordingly. Depending on the embryo species, the tests in the image analysis or machine vision software can be adjusted for detection of orientation.

EXAMPLES

Example 1

Construction of an Orientation and Sorting Device

An embryo reservoir for Norwegian spruce embryo was set up from which the embryos were fed through a flow loop into the orientation and sorting device.

The flow loop was constructed from a mixture of glass and Tygon tubing. A continuously variable peristaltic pump drew water and embryos from a reservoir through the separation section and into a pressurized chamber filled with air and water. This pressurized chamber served to dampen the pulsations associated with the peristaltic pump. This is a standard method to dampen the pulsation from a pump.

After leaving this chamber the water and embryos passed into and through the imaging section which was constructed of a 30 cm length of square borosilicate glass tubing with an inside cross-section nominally 3 mm across. On leaving the imaging section the flow entered a round Tygon tubing with 3 mm internal diameter and moved past a solenoid pinch valve (8), into the reorientation section (7), past another pinch valve (9) and on to its final destination (20) or (21) depending on the results from the tests A and B.

Imaging Setup and Embryo Analysis

Two photoelectric laser-based sensors were installed above the imaging section aiming downwards and sideways at a 90 degree configuration relative to each other, and both focused in the middle of the glass channel near the mid-point of the length. These sensors were set in the light-operate mode such that they each outputs a signal of 10 Volt when the optical path is clear and 0 Volt when an object breaks the laser beam. It was connected to the computer through the analog/digital (A/D) Input-Output (IO) board.

A Prosilica EC 650C camera with a Nikkor macro lens was mounted on the bench and focused immediately downstream of the sensor. This is a 3 CCD digital still and video camera shooing in 32 bit color at 640×480 resolution. The camera is connected to the computer via a firewire interface and is trigged with a TTL signal from the A/D I/O board. This signal trips the shutter while simultaneously triggering an external 160 W flash unit.

Once an object of sufficient size was determined to be in the imaging section the program initializes the camera, sends a signal to trigger the shutter and flash together, and transfers the captured image to the computer as a 32 bit RGB image file. The image was saved to disk with a time stamp for future references.

The background of the image was removed by subtracting a previously captured background image, leaving only the difference between the two images. The intensity plane was then extracted, effectively converting the image to pure grayscale, to improve computational speed. From the known top and bottom boundaries of the tube a region of interest (ROI) was defined.

The first task was to determine if an object was captured by the camera. To do this a horizontal clamp filter was applied, this searched for an object's left and right bound by looking for a sudden change in mean pixel intensity as computed over a vertical rake which progressed from the left and right edges toward the center of the image in the ROI.

If no object was found or only one which had too low of a reflectance to be an embryo, the image processing stopped and the system looked for the next object. If an object was found, its length was computed and compared to an operator set range. If the object was too long or too short to be of interest the image processing stopped and the system searched for the next object.

If the object was determined to be within the desired range for an embryo, two tests were applied to classify the embryo. A vertical clamp filter was used to determine object thickness at the left end, right end and midpoint. If the midpoint is substantially thicker or thinner than the average of the thicknesses of the two ends, that object was rejected as malformed. An edge finding filter is then applied, running top to bottom, on a three pixel rake at both ends. If no edges were detected on either end the object was rejected. If a similar number of edges were found on both ends, the object was rejected as having no clear crown end. If one end was found to have more than twice as many edges as the other then that end was determined to be the crown end. The processed image was then saved with a time stamp and with the image processing results embedded.

Computing and control unit tasks were handled on a Windows XP machine with an Intel 3 GHz dual core processor and 1 GB of RAM. Instrument interfacing was done through firewire (for the camera) and a Keithley KPCI-3116/3110 analog and digital interface board (for the sensors, camera, flash trigger and valves). The program is coded in G in the LabVIEW programming environment. Parts of the program may be converted to C/C++ for speed and portability. We used the then current version of LabVIEW (8.5) with the Real Time, IMAQ and NI Vision extensions from National Instruments, the iVision toolkit from HYTEK Automation and the Driver LYNX toolkit from Keithley. The software platform could vary from system to system. This technology is independent of the software application and can be programmed in various programming languages.

Software Test to Detect the Orientation of an Embryo

The detection of the embryo orientation was based on two tests, aspect ratio test (A) and edge detection test (B), as outlined below.

Test A examined the thickness of the embryo at both ends and the middle, the side with the larger thickness was assumed to be the crown. If the mid section was found to be thicker than both ends, then the embryo was rejected.

Test B examined the edge of the embryos to find the side with the crown.

If both tests A and B agreed, the program assigned a definite orientation and went to step (a). If tests A and B did not agree, the embryo was rejected.

The procedure consisted of the following steps:

Step (a): If the orientation was correct the embryo was deposited in reservoir (20). If the orientation was not correct, them the re-orientation part of the program was activated sending the embryo to be re-oriented, as disclosed above.

Operation Reversing the Orientation of an Embryo

Once leaving the imaging section, the object passed through Tygon tubing and past an Acro solenoid operated valve and into the glass reversing section. If the object was rejected it was allowed to pass through into a disposal reservoir, a beaker. If the object was determined to be a properly oriented embryo it was allowed to pass through and then was directed to a test tube. If the object was determined to be an improperly oriented but otherwise acceptable embryo the pinch valve immediately downstream of a Y-shaped glass tube (7) closed sending the embryo into the reservoir tube (5). After one second this valve opened and the upstream valve (8), between the imaging section and the Y-shaped glass tube (7) reversing section, closed for two seconds while gravity forced the embryo, now correctly oriented, back into the flow path. The upstream valve was then opened and the embryo was directed to the proper embryo receiver (20). The program then resumed looking for the next object in the imaging section.

Verifying the System with Norway Spruce Embryos

In one of many tests with different cell lines for Norway Spruce, 12 embryos out of the 50 embryos tested were detected and labelled as good mature embryos. The remaining embryos either had irregular shape or were immature embryos. The time required for processing each individual embryo was a fraction of a second. To determine timing, the image analysis program executed on its own dedicated processor core, image acquisition and transfer took about 10 ms as being hardware limited, subtracting the background and extracting intensity plane took less than 1 ms, scanning for objects and calculating length took less than 1 ms, test for thickness took less than 1 ms, and test for edges took less than 1 ms. Therefore, neglecting acquisition time, all analysis and tasks combined in series averaged about 1.5 ms.

The embryos that were smaller than the threshold (3 mm for Norway Spruce) in length as well as those embryos that did not have proper shape and aspect ratio were rejected. The embryos that were mature with proper shape were examined to determine their orientation. If the orientation was correct, the embryo was deposited in the test tube. If the orientation was not correct, then the embryo was sent to go through the re-orientation section of the loop, as disclosed above, prior to being deposited in the test tube.

In the test, the overwhelming majority of the embryos accepted exiting the apparatus were correctly oriented and viable.

Device for Collecting Correct Oriented Embryos.

A plate system ("Plate") with wells and openings for receiving acceptable and rejected embryos, respectively, was made and installed on a computer controlled x-/y-table. The wells will then work as embryo receiver (20) and the openings were used for water and rejected embryos (secondary destination (21)). The Plate was attached on an x-/y-table, which was controlled by the computer. When no embryo or a rejected embryo was detected, the table was located such that the flow was directed beside any well. When an acceptable embryo was detected, the table was located such that the embryo exited into a well. The software then noted the well as occupied. The subsequent embryos were always placed in a vacant wells using by relocating the x-/y-table accordingly.

The invention claimed is:

1. An apparatus for automatic orienting of plant embryos suspended in a liquid flowing through the apparatus, comprising
   a) flow channels for the liquid comprising a liquid inlet of an inlet tube, a liquid outlet of an outlet tube, a reservoir tube connected to a reservoir device, said reservoir device comprising means for generating positive liquid pressure in relation to the liquid pressure at outlet, means for accommodating liquid flowing in as well as means of providing liquid for outward flow, wherein the inlet tube, the outlet tube and the reservoir tube are connected at an intersection, and wherein the flow channels are dimensioned such that embryos may travel with the liquid flowing through the channels but are restricted to travelling either in a crown-first or crown-last orientation by dimensional constraints without a possibility to change orientation while travelling through any of the said tubes unless the change in orientation occurs as disclosed further below;
   b) a flow direction means comprising means of:
      i) directing the flow from the inlet to the outlet;
      ii) directing the flow from the inlet to the reservoir device; and
      iii) directing the flow from the reservoir device to the outlet;
   c) detector(s) comprising an orientation detector placed in the inlet tube, wherein the orientation detector comprises means of determining the orientation of an embryo passing through the inlet tube;
   d) a control unit for steering the flow of the liquid in the flow channels comprising means of receiving input from the orientation detector and means controlling the flow direction means such that:
      i) in a default position, when no embryo is detected by the orientation detector, the flow direction means is controlled such that the flow of the liquid in the flow channels is directed from the inlet to the outlet;
      ii) when an embryo having an orientation matching a predetermined orientation is detected by the orientation detector, the flow direction means is controlled such that the flow of the liquid in the flow channels is directed from the inlet to the outlet;
      iii) when an embryo having an orientation opposite to the predetermined orientation is detected by the orientation detector, the flow direction means is controlled such that the flow of the liquid in the flow channels is directed from the inlet toward the reservoir device so that the embryo enters the reservoir tube, after which the flow direction means is controlled such that the flow of the liquid in the flow channels is directed from the reservoir device to the outlet so that the embryo enters the outlet tube, after which the flow direction means is controlled such that the flow of the liquid in the flow channels is directed from the inlet to the outlet;

whereby all embryos suspended in the liquid exiting from the outlet will have an orientation matching the predetermined orientation.

2. The apparatus according to claim 1, additionally capable of sorting acceptable embryos from other objects, wherein
a) the flow direction means additionally comprise means of directing the flow into either an embryo receiver or a secondary destination;
b) the orientation detector additionally comprises means of separating acceptable embryo from other objects;
c) the control unit comprises additional means of controlling the flow direction means such that:
  i) in a default position, when no object is detected by the orientation detector, the flow direction means is controlled such that the flow of the liquid in the flow channels is directed from the inlet to the outlet and the outlet flow is directed into the secondary destination;
  ii) when an object other than an acceptable embryo is detected by the orientation detector, the flow direction means is controlled such that the flow of the liquid in the flow channels is directed from the inlet to the outlet and the outlet flow is directed into the secondary destination;
  iii) when an acceptable embryo having an orientation matching a predetermined orientation is detected by the orientation detector, the flow direction means is controlled such that the flow of the liquid in the flow channels is directed from the inlet to the outlet and the outlet flow is directed into the embryo receiver;
  iv) when an acceptable embryo having an orientation opposite to the predetermined orientation is detected by the orientation detector, the flow direction means is controlled such that the flow of the liquid in the flow channels is directed from the inlet to the reservoir device so that the embryo enters the reservoir tube, after which the flow direction means is controlled such that the flow of the liquid in the flow channels is directed from the reservoir device to the outlet so that the embryo enters the outlet tube, after which the flow direction means is controlled such that the flow of the liquid in the flow channels is directed from the inlet to the outlet and the outlet flow is directed into the embryo receiver;
whereby all acceptable embryos suspended in the liquid exiting from the outlet will be directed into the embryo receiver and will have an orientation matching the predetermined orientation and whereby other objects are sorted into the secondary destination.

3. The apparatus according to claim 1, wherein
a) the flow direction means comprise an inlet valve placed in the inlet tube and an outlet valve placed in the outlet tube, wherein said valves provide means of controlling the flow in the flow channels by opening and closing in response to control signals;
b) the control unit comprises means of controlling the inlet valve and the outlet valve such that:
  i) in a default position, when no embryo is detected by the orientation detector, the inlet valve is open and the outlet valve is open, whereby the flow of the liquid in the flow channels is directed from the inlet to the outlet;
  ii) when an embryo having an orientation matching a predetermined orientation is detected by the orientation detector, the inlet valve remains open and the outlet valve remains open, whereby the flow of the liquid in the flow channels remains directed from the inlet to the outlet; and
  iii) when an embryo having an orientation opposite to the predetermined orientation is detected by the orientation detector, the inlet valve remains open and the outlet valve is closed, whereby the flow of the liquid in the flow channels is directed from the inlet to the reservoir device so that the embryo enters the reservoir tube, after which the inlet valve is closed and the outlet valve is opened whereby the flow of the liquid in the flow channels is directed from the reservoir to the outlet so that the embryo to enters the outlet tube, after which the inlet valve is opened and the outlet valve remains open, whereby the flow of the liquid in the flow channels is again directed from the inlet to the outlet as in the default position;
whereby all embryos suspended in the liquid exiting from the outlet will have an orientation matching the predetermined orientation.

4. The apparatus according to claim 3, wherein the inlet valve and/or the outlet valve is a solenoid pinch valve.

5. The apparatus according to claim 1, wherein the apparatus further comprises one or more of the following:
(a) an additional reservoir tube detector comprising means of detecting the presence or absence of an embryo in the reservoir tube, and the control unit comprises means of receiving input from the reservoir tube detector to determine when an embryo has entered the reservoir tube by waiting for the reservoir tube detector to detect the presence and the location of an embryo in the reservoir tube; and/or
(b) an additional outlet tube detector comprising means of detecting the presence or absence of an embryo in the outlet tube, and the control unit comprises means of receiving input from the outlet tube detector to determine when an embryo has entered the outlet tube by waiting for the outlet tube detector to detect the presence and location of an embryo in the outlet tube.

6. The apparatus according to claim 1, wherein one or more cases when an object or an embryo is to enter a particular location is determined by a predetermined timing based on a constant flow rate of the liquid flowing through the apparatus.

7. The apparatus according to claim 1, wherein the reservoir device comprises a liquid container open to atmospheric pressure containing liquid having a surface level higher relative to the outlet such that the hydrostatic pressure is sufficient to provide liquid flow in the flow channels from the reservoir device to the outlet when the flow direction means are set accordingly.

8. The apparatus according to claim 7, wherein the reservoir device has a much larger horizontal cross-sectional area compared to the cross-sectional area of the reservoir tube, such that the level of liquid inside the reservoir is substantially constant during operation.

9. The apparatus according to claim 1, wherein the orientation detector further comprises a digital imaging means and image analysis means.

10. A computer program product for use in an apparatus according to claim 1, which comprises computer readable code means, which when run in a control unit for steering the flow of the liquid in the flow channels comprising means of receiving input from the orientation detector and means controlling the flow direction means such that:
  i) in a default position, when no embryo is detected by the orientation detector, the flow direction means is controlled such that the flow of the liquid in the flow channels is directed from the inlet to the outlet;
  ii) when an embryo having an orientation matching a predetermined orientation is detected by the orientation detector, the flow direction means is controlled such that the flow of the liquid in the flow channels is directed from the inlet to the outlet;
  iii) when an embryo having an orientation opposite to the predetermined orientation is detected by the orientation detector, the flow direction means is controlled such that the flow of the liquid in the flow channels is directed from the inlet toward the reservoir device so that the embryo enters the reservoir tube, after which the flow direction means is controlled such that the flow of the liquid in the flow channels is directed from the reservoir device to the outlet so that the embryo enters the outlet tube, after which the flow direction means is controlled such that the flow of the liquid in the flow channels is directed from the inlet to the outlet,
  causes the control unit to perform the action described in claim 1 associated with the control unit in response to the inputs to the control unit described in claim 1.

11. A computer program product for detecting the orientation of individual embryos in an apparatus according to claim 1 comprising computer readable code means, which when run in an orientation detector of the apparatus causes the orientation detector to perform the steps of:
  i) image acquisition;
  ii) image analysis; and
  iii) detecting the orientation of an embryo.

12. A computer program product according to claim 11, further comprising computer readable code means, which when run in an orientation detector of the apparatus causes the orientation detector to perform the step of:
  iv) determining the acceptability of an embryo.

13. A computer program product according to claim 12, wherein the step of detecting the acceptability of an embryo further comprises the steps of:
  i) examining the size of the embryo;
  ii) examining the thickness of the embryo at both ends and the middle, whereby the side with the larger thickness is deemed to be the crown; and
  iii) examining the edge of the embryos to find the side with the crown, wherein the side with more edges is deemed to be the crown;
  whereby embryos having size smaller than a threshold value, embryos having larger thickness at the middle than at both ends, and embryos giving conflicting results from the steps (ii) and (iii) as to the direction of the crown are deemed not acceptable.

14. A computer program product according to claim 11, wherein the step of detecting the orientation of an embryo further comprises one or more of the steps of:
  i) examining the thickness of the embryo at both ends and the middle, whereby the side with the larger thickness is deemed to be the crown; and/or
  ii) examining the edge of the embryo to find the side with the crown, wherein the side with more edges is deemed to be the crown.

* * * * *